United States Patent [19]
Janssen et al.

[11] Patent Number: 5,483,957
[45] Date of Patent: Jan. 16, 1996

[54] MEDICAL APPARATUS WITH CABLES EXTENDING BETWEEN ROTATABLE PARTS

[75] Inventors: Jozef T. A. Janssen; Theodorus J. M. Van Genechten, both of Eindhoven, Netherlands

[73] Assignee: U.S. Philips Corporation, New York, N.Y.

[21] Appl. No.: 338,918

[22] Filed: Nov. 14, 1994

[30] Foreign Application Priority Data

Nov. 12, 1993 [BE] Belgium ................ 09301252

[51] Int. Cl.⁶ ................ A61B 5/00; H05G 1/06
[52] U.S. Cl. ............ 128/630; 128/653.1; 378/194
[58] Field of Search .............. 128/630, 653.1, 128/660.01; 378/194; 439/212, 925

[56] References Cited

U.S. PATENT DOCUMENTS

| | | | |
|---|---|---|---|
| 3,541,334 | 11/1970 | Sobolewski | 378/194 |
| 4,157,472 | 6/1979 | Bech, Jr. et al. | 378/194 |
| 4,816,617 | 3/1989 | Valosen | 378/194 |
| 4,877,973 | 10/1989 | Torii et al. | 378/194 X |

FOREIGN PATENT DOCUMENTS

| | | |
|---|---|---|
| 0506172 | 9/1992 | European Pat. Off. . |
| 8101448 | 4/1982 | Netherlands . |

*Primary Examiner*—Francis Jaworski
*Attorney, Agent, or Firm*—Jack D. Slobod

[57] ABSTRACT

Medical apparatus includes a stand with an approximately L-shaped arm having a first portion (1) and a second portion (3) which extends approximately perpendicularly to the first portion and a free end of which supports at least one medical apparatus (7, 9). The first portion (1) has a free end which is connected, to, for example a floor (13) of an examination space via, a bearing (17), in such a manner that it can be rotated from a neutral position in opposite directions through an angle of Δ radians in a plane of rotation parallel to the floor. A bundle of cables (21) extends from a space (19) at the side of the floor (13) which is remote from the examination space to parts of the device. The bundle of cables (21) is shaped approximately as a flat ribbon having a largest thickness t equal to the thickness of the thickest cable and a width w equal to the sum of the thicknesses of the cables. The bundle (21) extends to the free end of the second portion via an opening (25) in the floor (13) at the area of the bearing (17) and a cavity (29) formed in the arm (1, 3) and extending over the entire length of the arm. The cavity (29) has an approximately rectangular cross-section with a width which equals at least w and a height which equals at least t, the width direction of the cavity in the first portion (1) of the arm extending substantially parallel to the floor surface. The cables of the bundle (21) are secured in a first cable holder (23) which is situated at the side of the bearing (17) which is remote from the second portion (3) of the arm and which defines the positions of the cables relative to one another. At the area of the transition between the first portion (1) and the second portion (3) of the arm there is provided a protrusion (31), so that the height of the cavity (29) in the second portion of the arm locally equals at least $t+\alpha w$.

4 Claims, 3 Drawing Sheets

5,483,957

MEDICAL APPARATUS WITH CABLES EXTENDING BETWEEN ROTATABLE PARTS

BACKGROUND OF THE INVENTION

The invention relates to a medical apparatus, comprising a stand with an approximately L-shaped arm which comprises a first portion having a free end which is connected, via a bearing, to a boundary surface of an examination space in such a manner that it can be rotated from a neutral position into opposite directions through an angle of α radians in a plane of rotation which is parallel to said boundary surface, and also comprises a second portion which extends approximately perpendicularly to the first portion and to a free end of which there is attached at least one medical apparatus, a bundle of cables extending from a space at the side of the boundary surface which is remote from the examination space to parts of the apparatus.

An apparatus of this kind is known, for example from EP-A-0 506 172 (PHN 13.642). The boundary surface may be, for example the floor or the ceiling of the examination space. In the known apparatus an X-ray source and an X-ray detector, for example an X-ray image intensifier tube, are attached to the free end of the second portion via a support. The support may be, for example a C-arc which is rotatably connected to the free end of the second portion of the arm. The X-ray source and the X-ray detector are attached to oppositely situated ends of the C-arc. The bundle of cables comprises, for example power supply cables for powering the apparatus, tubes for the supply of cooling liquid and signal cables for transmitting instructions to the apparatus and for transferring measurement signals from the apparatus to processing equipment installed elsewhere. The cables preferably extend in a cable trough provided behind the boundary surface. In the known apparatus the cables extend freely, or via ornamental tubes, from the boundary surface to the relevant parts of the apparatus. The cables and ornamental tubes extending freely through the examination space, however, are not only unhygienic and ugly but also interfere with personnel attending the apparatus. The latter is the case notably when said boundary surface is the floor of the examination space. The cables are then spread across the floor so that an operator could easily trip over the cables.

It is an object of the invention to provide an apparatus of the kind set forth in which the cables can extend almost invisibly from the boundary surface to the relevant parts of the apparatus. To achieve this, the apparatus in accordance with the invention is characterized in that the bundle of cables is shaped as an approximately flat ribbon having a largest thickness t equal to the thickness of the thickest cable of the bundle and a width w equal to the sum of the thicknesses of the cables, and extends to the free end of the second portion via an opening in the boundary surface at the area of the bearing and a cavity formed in the arm and extending over the entire length of the arm, said cavity having an approximately rectangular cross-section of a width which at least equals w and a height which at least equals t, the width direction of the cavity in the first portion of the arm extending substantially parallel to the boundary surface, the cables of the bundle being secured in a first cable holder which is situated at the side of the bearing remote from the second portion of the arm and defines the positions of the cables relative to one another. and that at the area of the transition between the first and the second portion of the arm there is provided a protrusion so that the height of the cavity in the second portion of the arm locally equals at least t+αw.

The entire bundle of cables now extends through the tubular cavity in the arm. Because the bundle is shaped as a flat ribbon, the transverse dimensions of the arm need not be larger, or only hardly larger, than required already for constructional reasons. During rotation the ribbon of cables is forced to make a bend, so that the cables situated at the outer side are pulled and the cables situated further inwards are pushed back. The protrusion serves to accommodate the cable slack thus occurring, so that the cable bundle as a whole retains the shape of a flat ribbon and the cables are not damaged.

It is to be noted that NL-A-81 01 448 discloses a medical apparatus with a pivot arm in which cables extend. In this apparatus, however, the pivot arm is not L-shaped and, moreover, the transverse dimension of the pivot arm is comparatively large because the arm must be provided with cavities having a substantially square cross-section for the cables.

A preferred embodiment of the apparatus in accordance with the invention is characterized in that near the protrusion in the second portion of the arm, there is provided a second cable holder which defines the positions of the cables relative to one another. The movement of the cables relative to one another, caused by rotation of the arm, is thus limited to the part of the bundle of cables extending between the two cable holders.

A further preferred embodiment of the apparatus in accordance with the invention is characterized in that the bundle of cables extends through an opening formed in the ring-shaped bearing. As a result of this step, the height of the arm at the area of the bearing may be minimum, thus minimizing the volume occupied by the apparatus.

BRIEF DESCRIPTION OF THE DRAWING

These and other aspects of the invention will be described in detail hereinafter with reference to the drawing.

DETAILED DESCRIPTION OF THE PREFERRED EMBODIMENTS

Figure 1:
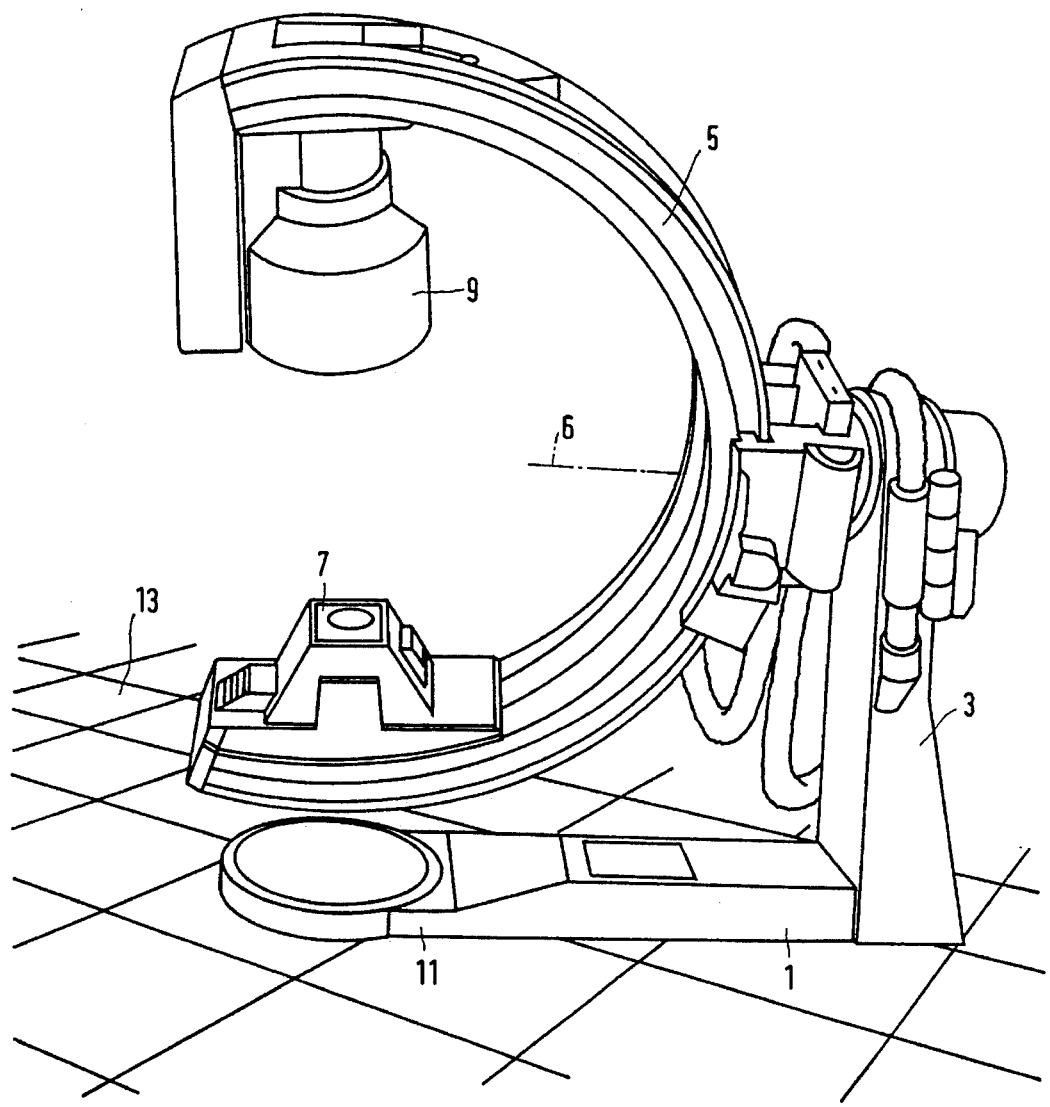
FIG. 1 is a perspective view of an embodiment of an apparatus in accordance with the invention.

The apparatus shown in FIG. 1 comprises a stand with an approximately L-shaped arm which comprises a first portion 1 and a second portion 3 which extends approximately perpendicularly thereto. A support 5 in the form of a C-arc is attached to the free end of the second portion 3. The C-arc 5 is rotatable about a horizontal axis 6 relative to the second portion 3. Near one end of the C-arc 5 there is arranged an X-ray source 7, whereas near its other end there is arranged an X-ray detector 9, for example an X-ray image intensifier tube. The X-ray source 7 and the detector 9 are mounted on the C-arc 5 so as to face one another, with the result that a radiation beam emitted by the X-ray source reaches the detector via an object (for example a patient which is not shown) arranged between the arms of the C-arc. Thus, this embodiment of the apparatus is suitable for making X-ray image of the patient. Evidently, the support 5 may also have a different shape, for example the shape of a parallelogram as is also known from the cited document EP-A-0 506 172. Moreover, the support 5 may be completely absent. Other medical apparatus, for example ultrasound equipment or radiation therapy equipment may also be attached to the support (or directly to the free end of the second portion 3 of the arm).

The first portion 1 of the arm comprises a free end 11 which is connected, via a bearing (not visible in FIG. 1), to a floor 13 of an examination space. Via the bearing, the first portion 1 can rotate from a neutral position in opposite directions through an angle of $\alpha$ radians. The first portion 1 then remains parallel to the floor 13. The apparatus can similarly be secured to another boundary surface of the examination space, for example to the ceiling or a wall.

Figure 2:
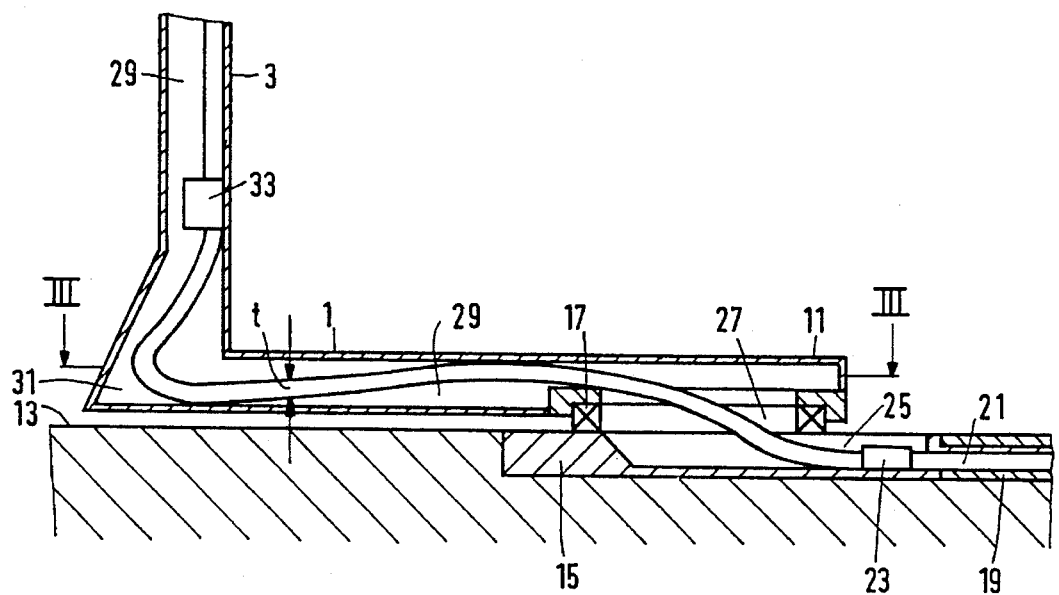
FIG. 2 is a diagrammatic longitudinal sectional view of a part of an L-shaped arm of the apparatus shown in FIG. 1.

FIG. 2 is a longitudinal sectional view of a portion of the L-shaped arm, the first portion 1 being completely visible whereas the second portion 3 is only partly visible. The free end 11 of the first portion 1 is secured to the floor 13 by way of a floor plate 15. To this end, the floor plate 15 is accommodated in the floor so that its upper surface is substantially flush with the floor surface. On the floor plate 15 there is mounted a ring-shaped bearing 17 which constitutes the connection between the floor plate and the first portion 1 of the arm. This bearing enables rotation of the first portion in a plane parallel to the floor 13. The angle $\alpha$ wherethrough the first portion can be rotated from the neutral position is limited to a predetermined value, for example to $\pi/2$ radians in both directions, by stops (not shown). Underneath the surface of the floor 13 there is provided a cable trough 19 in which a bundle of cables 21 extends. The bundle 21 comprises, for example current cables for the supply of electric energy, ducts for a cooling liquid, and signal leads for controlling parts of the apparatus and for transporting signals generatext, for example by the X-ray detector 9.

Figure 3:
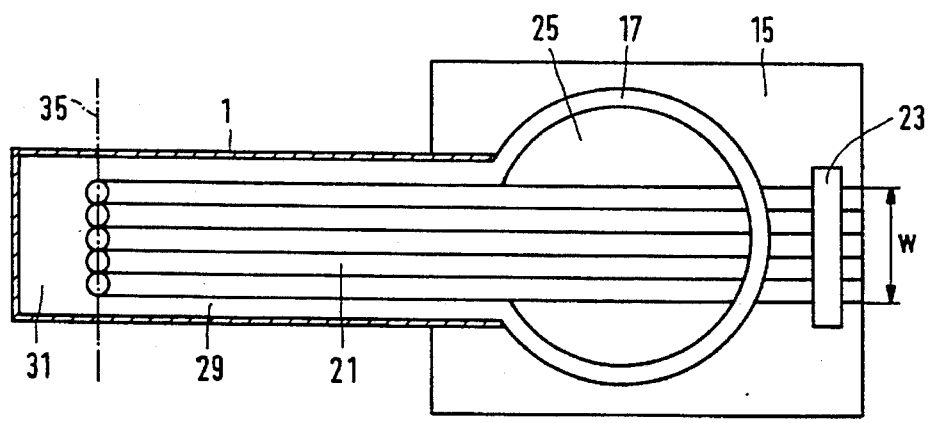
FIG. 3 is a diagrammatic sectional view, taken along the line III—III, of the part shown in FIG. 2 in a first position of the arm.

FIG. 3 shows that the cables in the bundle 21 are adjacently arranged so that the bundle is shaped approximately as a flat ribbon whose width equals w and whose largest thickness (see FIG. 2) equals t. The value of t is determined by the thickness of the thickest cable in the bundle 21 and the value of w is determined by the sum of the thicknesses of the cables. The ribbon-like shape of the cable bundle is maintained by the presence of a first cable holder 23 which is situated on the floor plate 15 at the side of the bearing 17 which is remote from the second portion 3 of the arm, i.e. at the right-hand side of the bearing in the FIGS. 2 and 3. The first cable holder 23 may consist of, for example two strip-like parts wherebetween the cables are clamped, or of a strip-shaped holder whereto a tie tag is attached for each cable so as to secure the cable to the holder. The first cable holder 23 defines the positions of the cables relative to one another so that the cable bundle 21 is ribbon-shaped at least in the vicinity of this cable holder.

Figure 4:
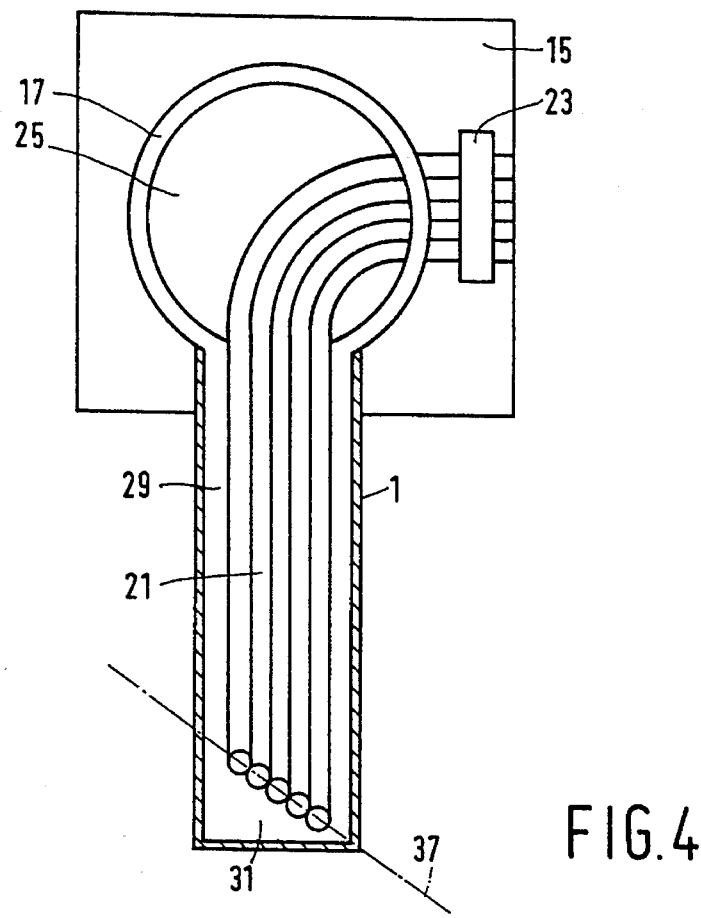
FIG. 4 is a sectional view, corresponding to FIG. 3, in a second position of the arm.

From the cable trough 19 the cable bundle 21 extends, via an opening 25, defined by the floor plate 15, in the floor surface and an opening 17 formed in the ring-shaped bearing 17, to a cavity 29 which extends over the entire length of the arm 1, 3. This cavity has an approximately rectangular cross-section with a width which equals at least w and a height which equals at least t. At the area of the transition between the first portion 1 and the second portion 3 of the arm there is provided a protrusion 31 whose function will be described in detail hereinafter. In the second portion 3 of the arm preferably a second cable holder 33 is provided in the vicinity of the protrusion 31, which second cable holder defines the positions of the cables in the bundle 21 relative to one another. The second cable holder 33 may have the same shape as the first cable holder 23. In the immediate vicinity of the first and second cable holders 23, 33 the positions of the cables in the bundle 21 relative to one another are rigidly defined, whereas some movement is possible in the region between the two cable holders. This freedom of movement is necessary because during rotation of the arm around the bearing 17 the cables are bent with different radii of curvature which are dependent on their position in the bundle 21. The cables bent with the largest radius of curvature are then pulled whereas the cables bent with the smallest radius of curvature are pushed back. As a result of the freedom of movement of the cables, damaging of the cables is prevented and the bundle 21 is distorted instead near the transition between the first portion 1 and the second portion 3 of the arm. In the neutral position, shown in FIG. 3, all cables extend over substantially the same length in the longitudinal direction of the first portion 1. The bending points, where the cables are bent at right angles to the second portion 3, are then also situated on a line 35 extending transversely of the longitudinal direction of the first portion 1. When the arm 1, 3 has been rotated through a right angle, as shown in FIG. 4 these bending points are situated on a line 37 which encloses an angle relative to the longitudinal direction of the first portion 1. The ribbon-shaped cable bundle 21 is then bent at the area of the bearing 17 and the bending points of the cables situated further inwards in the bend are pushed away from the bearing whereas the bending points of the cables situated further outwards are drawn towards the bearing. This movement of the bending points is possible because on the one hand, as has already been stated, the cables exhibit a given freedom of movement relative to one another in the relevant part of the bundle 21, and on the other hand sufficient space is available in the protrusion 31 to take up the displacements of the bending points.

Figure 5:
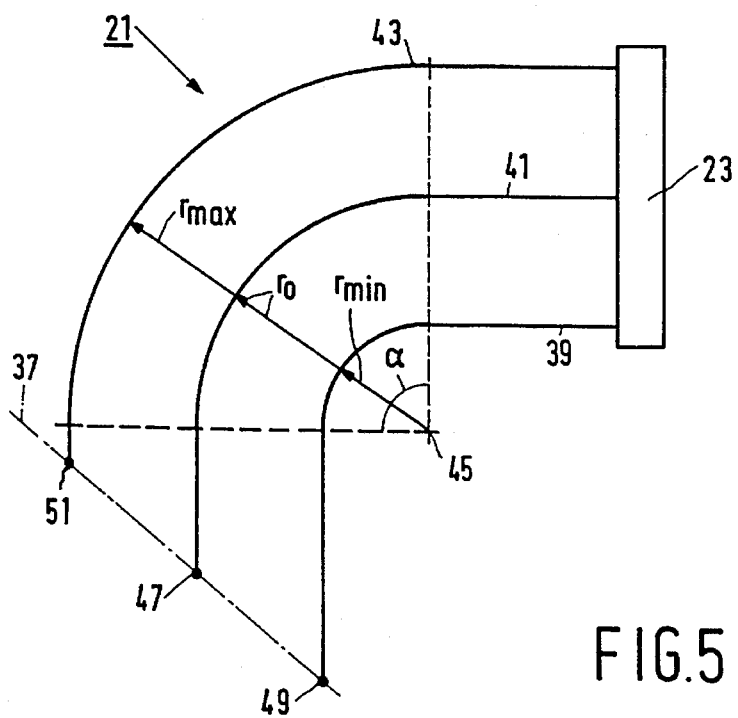
FIG. 5 is a diagrammatic representation of the course of a part of the cables in FIG. 4.

FIG. 5 shows diagrammatically the course of some cables in the bundle 21. The minimum size of the protrusion 31 will be calculated on the basis of this Figure. The Figure shows diagrammatically the course of the inner cable 39, the central cable 41 and the outer cable 43 in the ribbon-like cable bundle 21 bent around a centre of curvature 45. The radii of curvature of these three cables are denoted by the references $r_{min}$, $r_0$ and $r_{max}$, respectively. The angle $\alpha$ wherethrough the bundle 21 is bent then equals $\pi/2$ radians. Upon bending the central cable 41 assumes a central position so that the position of the bending point 47 does not change. The length of the bent part of this cable equals $\alpha r_0$. Therefore, this is a standard length with which the lengths of the bent parts of the other cables in the bundle 21 can be compared. The length of the bent part of the inner cable 39 is $\alpha r_{min}$ and the length of the bent part of the outer cable 43 is $\alpha r_{max}$. The bending point 49 of the inner cable 39, therefore, will be pushed away from the bearing 17 over a distance $\alpha(r_0 - r_{min})$ and the bending point 51 of the outer cable 43 will be drawn towards the bearing over a distance $\alpha(r_{max} - r_0)$. The bending points of the intermediate cables will be displaced over smaller distances.

In the FIGS. 4 and 5 it has been assumed that the arm has been rotated counterclock-wise relative to the neutral position shown in FIG. 3. When the arm is rotated clock-wise from the neutral position, the cable 43 becomes the inner cable and the cable 39 becomes the outer cable. It follows therefrom that the bending points of the two cables 39 and 43 at the edges of the bundle 21 must be displaceable over a distance $\alpha(r_{max}-r_{min})$. Because $r_{max}-r_{min}$w, the total space available for displacement of The bending points must be equal to $\alpha$.w. This space must be added to the space available to the thickness t of the cable bundle 21 in the portion of the cavity 29 which extends in the second portion 3 of the arm. The protrusion 31, therefore, will have to be proportioned so that at the area of the protrusion the height of the cavity 29 in the second portion 3 of the arm equals at least t+$\alpha$w.

Evidently, modifications are feasible for the described embodiments. For example, the cable bundle 21 can also be guided via an opening in the extreme right-hand end of the first portion 1 of the arm in FIG. 2 instead of via the opening in the ring-shaped bearing 17. The bundle 21 will then be guided out of the floor 13 via an opening situated to the right of the bearing 17. However, this has the drawback that a part, be it a short part, of the cable bundle 21 will then extend on the floor 13 in the vicinity of the first end 11 of the first portion of the arm. Moreover, the height of the first portion 1 of the arm at the area of the bearing 17 must then be larger than in the embodiment shown.

We claim:

1. A medical apparatus, comprising a stand with an approximately L-shaped arm, which comprises a first portion (1) having a free end which is connected, via a bearing (17), to a boundary surface (13) of an examination space in such a manner that it can be rotated from a neutral position into opposite directions through an angle of $\alpha$ radians in a plane of rotation which is parallel to said boundary surface, and also comprises a second portion (3) which extends approximately perpendicularly to the first portion and to a free end of which there is attached at least one medical apparatus (7, 9), a bundle of cables (21) extending from a space (19) at the side of the boundary surface which is remote from the examination space to parts of the apparatus, characterized in that the bundle of cables (21) is shaped as an approximately flat ribbon having a largest thickness t equal to the thickness of the thickest cable of the bundle and a width w equal to the sum of the thicknesses of the cables, and extends to the free end of the second portion, via an opening (25) in the boundary surface (13) at the area of the bearing (17) and a cavity (29) formed in the arm (1, 3) and extending over the entire length of the arm, said cavity having an approximately rectangular cross-section of a width which at least equals w and a height which at least equals t, the width direction of the cavity in the first portion (1) of the arm extending substantially parallel to the boundary surface, the, cables of the bundle being secured in a first cable holder (23) which is situated at the side of the bearing remote from the second portion (3) of the arm and defines the positions of the cables relative to one another, and that at the area of the transition between the first and the second portion of the arm there is provided a protrusion (31) so that the height of the cavity in the second portion of the arm locally equals at least t+$\alpha$w.

2. An apparatus as claimed in claim 1, characterized in that near the protrusion (31) in the second portion (3) of the arm there is provided a second cable holder (33) which defines the positions of the cables relative to one another.

3. A device as claimed in claim 1, characterized in that the bundle of cables (21) extends through an opening (27) formed in the ring-shaped bearing (17).

4. A device as claimed in claim 2 characterized in that the bundle of cables extends through an opening formed in the ring-shaped bearing.

* * * * *